United States Patent [19]

Oddo

[11] 4,176,545
[45] Dec. 4, 1979

[54] ELECTRONIC ENGINE WEAR DETECTOR

[76] Inventor: Luigi G. Oddo, Rte. 2, Box 270, Palm Bay, Fla. 32905

[21] Appl. No.: 916,295

[22] Filed: Jun. 16, 1978

[51] Int. Cl.² ............................................. G01N 33/30
[52] U.S. Cl. .......................................... 73/64; 73/116; 324/71 CP
[58] Field of Search ................. 324/71 CP, 59; 73/64, 73/38, 61 R, 116; 210/85; 55/274

[56] References Cited

U.S. PATENT DOCUMENTS

| 2,252,222 | 8/1941 | Van Os | 324/71 CP |
| 2,741,741 | 4/1956 | Adams, Jr. | 324/59 |
| 3,457,504 | 7/1969 | Arthur et al. | 73/61 R X |
| 3,502,970 | 3/1970 | Thayer | 73/64 X |
| 3,878,103 | 4/1975 | Miller et al. | 210/85 X |

*Primary Examiner*—Jerry W. Myracle

[57] ABSTRACT

This application discloses an apparatus and electrical system for sensing the wear within an engine by detecting the presence of metal pieces which have become dislodged from the engine. The metal pieces are detected by collecting them upon a filter which is located generally within an inductor. The permeability of the inductor is measured as a function of the inductance, and the inductance becomes a measure of the number of particles collected by the filter.

8 Claims, 3 Drawing Figures

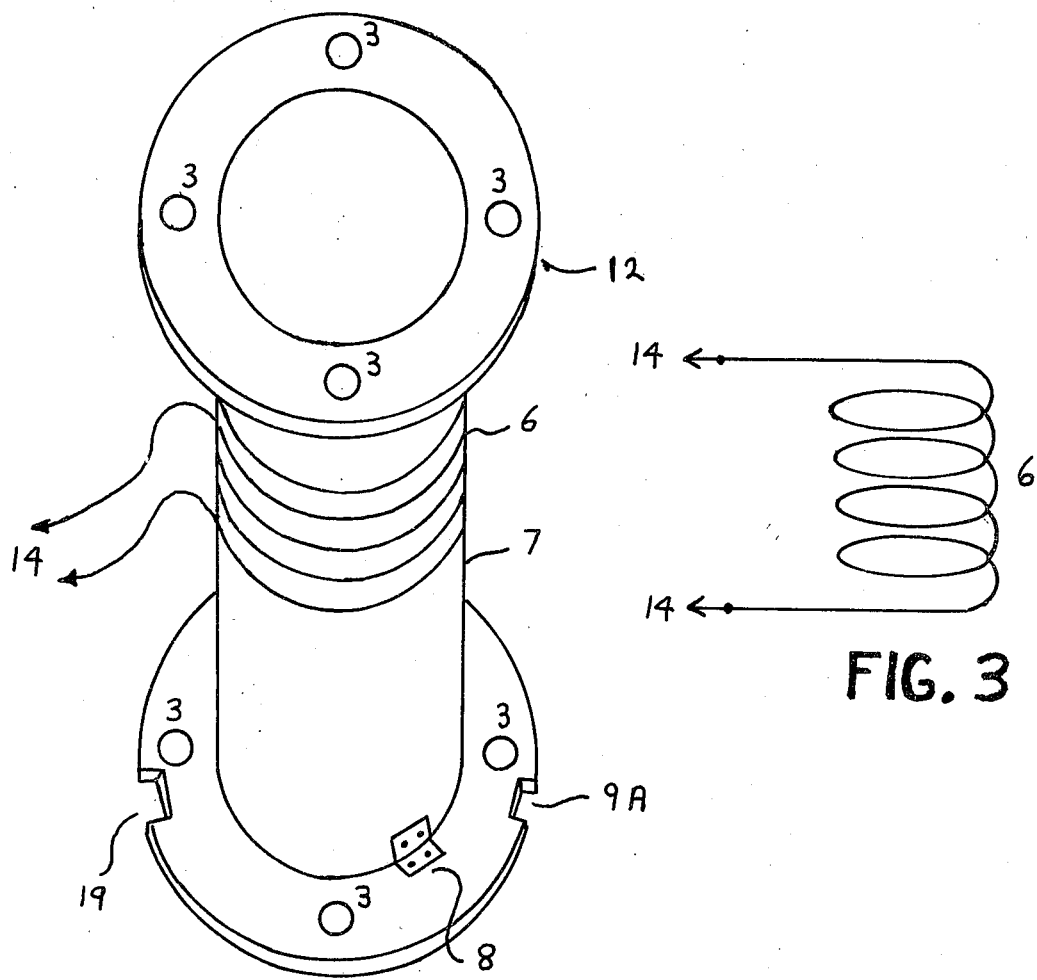

ELECTRONIC ENGINE WEAR DETECTOR

BACKGROUND OF THE INVENTION

I. Field of the Invention

The present invention relates to metallic engines and more specifically to electronic systems for detecting engine wear by collecting and analyzing metal chips therefrom.

II. DESCRIPTION OF THE PRIOR ART

Electronic engine wear detectors are well known in the prior art. These detectors may be divided into classes of capacitance type detectors, pressure type detectors and continuity type detectors. The capacitance type detectors sense the change in the dielectric constant between elements of a capacitor caused by the deposition of engine wear particles therebetween. These electronic systems are often very complicated and expensive to produce. The pressure type systems measure the flow pressure exerted by the flow of fluid over the filter and indicate when the filter becomes clogged. The continuity type detectors employ adjacent alternately polarized screen conductor elements which are shorted together by contact from metal particles representing engine wear.

The present invention is completely different from any of the above three (3) types of engine wear detectors in that it employs an inductance which changes value when the metal particles are deposited within the core of the inductance.

PURPOSE

The present device consists of an instant engine wear indicator designed to be inserted into the oil system of an engine. The device collects metal particles which are deposited upon a plastic strainer located inside an oscillator coil, thereby trapping the metal particles inside the coil. The metal grindings deposited upon the plastic strainer are detected by sensing the change in the permeability of the inductor. The inductor is connected to an oscillator and R.F. circuits and tuned to operate as an amplifier. A milliammeter is connected to the output of the amplifier. The accummulation of metal particles from within the oscillator coil causes a direct reading on the meter dial, thereby indicating engine wear from normal to emergency level conditions. A second test coil is built into the amplifier in order to check the amplifier and to verify the emergency reading by switching to the test coil. This device will provide a visual reading of the engine operating condition while the engine is in actual operation. The device is applicable to most engines.

SUMMARY OF THE INVENTION

The present invention includes an apparatus for detecting particles in a fluid stream. A first chamber or housing is provided for receiving and guiding the fluid stream therethrough. A strainer or filter means is interposed within the first chamber for collecting on an exposed surface thereof the particles while enabling the flow of the fluid therethrough. An inductance means is provided for sensing the changes in the permeability of the area adjacent to the filter means corresponding to the collection of the particles on the exposed surface thereof. Circuit means are coupled to the inductance means for displaying the relative inductance or permeability thereof so as to indicate the relative presence of the particles on the filter means.

BRIEF DESCRIPTION OF THE DRAWINGS

Other objects, features and advantages of the present invention will be apparent from a study of the written description and the drawings in which:

FIG. 2 illustrates a top perspective view of the tubular fluid guide and the coil wound therearound.

FIG. 3 illustrates a schematic representation of the inductance coil which is wound around the tubular flow guide member as illustrated in FIG. 2.

DETAILED DESCRIPTION OF THE INVENTION

Figure 1:
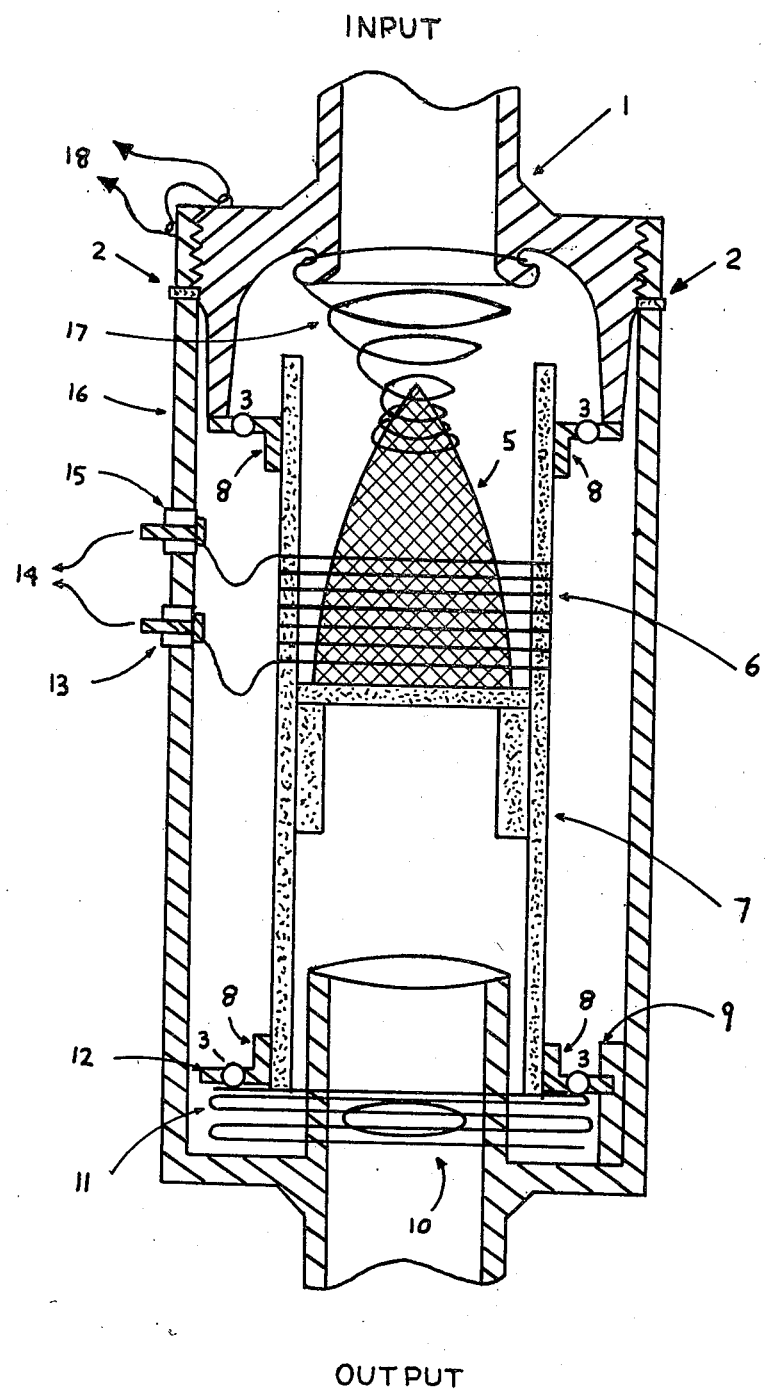
FIG. 1 illustrates a central cross-sectioned view of the present invention for revealing the construction of the housing, the fluid guide, the filter means, and the input and output ports.

A first preferred embodiment of the present invention is illustrated in FIG. 1. The device includes a cast metal housing 16 of approximately 3 inches in diameter and 6½ inches in length. An output pipe is illustrated as being unitary with the housing. The housing may be constructed in various sizes coordinated to particular engine oil circulation requirements. The dimension provided above is suitable for most engine oil system capacities. An oil strainer or filter, illustrated generally as 5, consists of a heat resistant plastic material. A generally cylindrical and hollow tubular element 7 is provided with an inner ledge to support the oil filter 5. The cylindrical tubing is manufactured of a heat resistant plastic.

An oscillator coil, illustrated generally as 6, is manufactured of a continuous copper wire wound around or possibly embedded within the tubing 7. The oscillator coil 6 is matched to the amplifier R.F. input or the I.F. input for proper frequency coupling. The base 12 of the tube 7 has a lip containing multiple holes on the top and bottom which are used for bypassing oil outside of the tube. A notch 19 provides assembling and disassembling clearance between the coil assembly 6 and the housing 16. A notch 9A provides a locking function for positioning the coil 6 within the housing 16. The inside of the housing 16 includes a guide 9 in order to lock the coil assembly from turning side to side.

The elements 13, 14 and 15 consist of insulators manufactured from a heat resistant insulated material which are threaded or pressed through the housing 16 in order to withstand the oil pressure from within. Two holes 10 are provided on the output pipe in order to provide for an oil bypass. A metal angle or gussett plate 8 is secured to the coil 7 for maintaining its proper position within the housing 16.

A spring 11 is provided to hold the coil assembly, comprising the tubing 7 and the coil 6, in proper position within the housing 16. A heat resistance plastic oil cap, illustrated generally as 2, is also provided at the top end of the housing 16.

A fine conical spring, illustrated generally as 17, is secured inside of the top housing cap, illustrated generally as 1, for restraining the filter 5 within its planned location inside the tubing 7. The cap 1 includes fine screw type threads for mating with the housing 16. Multiple rings, illustrated generally as 18, are attached to the outside of the housing and the cap in order to allow for the installation of safety wire when the device is assembled.

The invention may be assembled as follows. First, install the spring 11 within the bottom of the housing 16. Then, install the coil assembly 6 and 7 within the housing 16 and solder the output wires 14 to the appropriate connectors 14A. The wires 14 must be long enough to permit removal of the coil assembly 6 and 7 for periodical cleaning without the need to disconnect the wires from the connectors. Next, insert the coil assembly 6 and 7 over the bottom spring so that the match point 9A corresponds with the support 9 in order to lock the coil assembly into position within the housing. Next, insert the oil strainer or oil filter 5 within the coil assembly 6 and 7.

The gasket 2 is then inserted inside the pipe cap 1, and then the pipe cap and the spring assembly 17, having first been properly aligned, are coupled onto the housing 16. Safety wires 18 may be installed between the cap 1 and the housing 16. It is important for the operator to then check the housing for any oil leaks.

The filter or strainer element 5 should be cleaned or replaced every 200 hours or less in order to assure proper operation of this device. Next, the oscillator coil 6 should be connected through the wires 14 to the amplifier unit (not shown in the drawing for clarity). The amplifier and R.F. circuits are well known in the art, and are typically of the type employing a known capacitance with the variable inductance in order to change the output frequency dependent upon the value of the inductance present. A second inductance is also provided for calibrating the performance of the device.

The device is now ready to monitor engine wear by having the operator monitor the level of the millammeter connected to the output of the amplifier stage. The milliammeter is marked in engine wear units from normal to emergency wear which corresponds to the level of metal buildup on the oil filter or strainer. The second twin coil may be built into the amplifier test section for testing the proper functioning of the circuit and also to verify readings from the coil which is used in service, thereby alerting the operator of a true engine wear malfunction condition.

In accordance with the provisions of the United States Patent Laws, the preferred embodiment of the present invention has been described in detail. The principles of the present invention have been described in the best mode in which it is now contemplated that such principles may be applied. However, it should be understood that the construction shown and described in the attached specification and the drawings are merely illustrative and that the invention is not limited thereto. Accordingly, alterations and modifications which readily suggest themselves to persons skilled in the art, without departing from the true spirit of the disclosure herein, are intended to be included in the scope of the following claims.

I claim:

1. An apparatus for detecting particles in a fluid stream, comprising in combination:
    a housing for receiving and guiding the fluid stream therethrough;
    filter means interposed within said housing for blocking and collecting on an exposed surface thereof the particles while enabling the flow of the fluid therethrough;
    inductance means for sensing the changes in the permeability of the area adjacent to said filter means corresponding to the collection of the particles on said exposed surface thereof; and
    circuit means coupled to said inductance means for displaying the permeability thereof so as to indicate the relative presence of the particles on said filter means.

2. The detection apparatus as described in claim 1 wherein the particles have metallic properties and wherein the inductance of said inductance means increases responsive to the collection of the particles on said exposed surface of said filter means.

3. The detection apparatus as described in claim 1 wherein said inductance means comprises a coil having a generally open center section for generally surrounding at least a section of said exposed surface of said filter means.

4. The detection apparatus as described in claim 3 wherein said inductance means further includes a generally tubular section having said coil wound therearound.

5. The detection apparatus as described in claim 4 wherein said tubular section includes a generally open passageway having said filter means attached therein, with said tubular section for guiding the flow of the fluid over said filter means.

6. The detection apparatus as described in claim 5 wherein said filter means is generally conical with a tapering diameter oriented generally against the direction of flow of the fluid through said tubular member.

7. The detection apparatus as described in claim 6 wherein the section of said filter means adjacent said coil is of a larger diameter which is nearly equivalent to the inside diameter of said coil, whereby the collection particles will be juxtaposed with said coil.

8. The detection apparatus as described in claim 1 further including fluid bypass means within said housing for enabling the flow of the fluid around said filter means responsive to said filter means becoming obstructed.

* * * * *